United States Patent [19]

Dileo et al.

[11] Patent Number: 4,950,822

[45] Date of Patent: * Aug. 21, 1990

[54] OLEFIN OLIGOMER SYNLUBE PROCESS

[75] Inventors: Thomas J. Dileo; Marshall B. Nelson; Matthew J. Lynch, all of Baton Rouge, La.

[73] Assignee: Ethyl Corporation, Richmond, Va.

[ * ] Notice: The portion of the term of this patent subsequent to Jun. 19, 2007 has been disclaimed.

[21] Appl. No.: 212,018

[22] Filed: Jun. 27, 1988

[51] Int. Cl.$^5$ ............................................... C07C 2/00
[52] U.S. Cl. .................................... 585/310; 585/329; 585/525; 585/520; 585/521; 585/717; 585/719; 585/326
[58] Field of Search ............... 585/310, 329, 525, 520, 585/521, 717, 719, 326

[56] References Cited

U.S. PATENT DOCUMENTS 3,763,244 10/1973 Shubkin ............................... 585/525
4,436,947 3/1984 Morganson et al. ................. 585/525

*Primary Examiner*—Chung K. Pak
*Attorney, Agent, or Firm*—Joseph D. Odenweller

[57] ABSTRACT

Unsaturated α-olefin oligomers are topped to remove monomer and dimer and then distilled to remove a trimer fraction leaving a residue of tetramer, pentamer and higher oligomers. The trimer fraction is hydrogenated to form saturated α-olefin oligomer suitable for use as a lubricant.

3 Claims, No Drawings

OLEFIN OLIGOMER SYNLUBE PROCESS

BACKGROUND

Alpha-olefin oligomers and their use as synthetic lubricants ("synlubes") are well-known. Early reports of such synlubes are in Seger et al. U.S. Pat. No. 2,500,161 and Garwood U.S. Pat. No. 2,500,163. U.S. Pat. No. 2,766,312 describes the oligomerization of α-olefins in a Group IV metal oxide bed using a BF$_3$ promoter catalyst. Promoters include water, alcohol and ether.

U.S. Pat. No. 3,149,178 describes the preparation of a synlube by oligomerizing a C$_{6-12}$ α-olefin thermally or using a Friedel Crafts or peroxide catalyst followed by distillation to remove dimer. The distillation residue is hydrogenated for use as a synlube. U.S. Pat. No. 3,382,291 discloses a BF$_3$-promoter (e.g. alcohol) process for making α-olefin oligomers in which the BF$_3$ is used to saturate the α-olefin feed and a second stream of BF$_3$-promoter is fed to the reaction.

Cupples U.S. Pat. Nos. 4,045,507 and 4,045,508 describe a continuous process of oligomerizing α-olefins using a BF$_3$-alcohol system.

Use of hydrogenated oligomers as synlubes depends to a large extent on the viscosity of the hydrogenated oligomer. A large market exists for what is called a 4 cs (centistoke) synlube. These have a viscosity close to 4 cs at 100° C. (e.g. 3.6–4.2 cs). Attempts have been made to make 4 cs synlubes from α-decene oligomer by topping the crude unsaturated oligomer to remove monomer and dimer followed by hydrogenation of the residue which consists mainly of trimer, tetramer and higher oligomers. These fluids generally have viscosities that are too high to qualify as 4 cs synlubes. Attempts to distill this saturated oligomer to obtain a mainly trimer fraction having the proper viscosity, flash point, volatility and bromine number have encountered problems apparently due to thermal cracking of the hydrogenated oligomer during distillation. Accordingly a need exists for a process that can consistently make a saturated, mainly trimer α-olefin oligomer having the required viscosity, volatility, flash point and bromine number required for a successful synlube.

SUMMARY OF THE INVENTION

It has now been discovered that a low-viscosity synlube fraction having a high flash point, low volatility and low bromine number can be made from a crude unsaturated α-olefin oligomer containing monomer, dimer, trimer, tetramer and higher oligomers by distilling the monomers and dimers to obtain a dimer-free unsaturated oligomer, distilling a low viscosity mainly trimer fraction from the unsaturated oligomer and subsequently hydrogenating the low viscosity fraction to obtain a saturated low-viscosity synlube fraction having the above improved properties.

DESCRIPTION OF THE PREFERRED EMBODIMENTS

Methods for making the crude unsaturated α-olefin oligomer are well-known. A preferred method uses a promoted BF$_3$ catalyst in which the promoter is water, alcohol, organic ester, carboxylic acid, ketone, and the like. Of these the preferred promoters are water and alcohol, e.g. isopropanol, n-butanol, isobutanol, n-hexanol, 2-ethylhexanol, n-decanol and the like. In one mode of operation a small amount of the promoter, e.g. 0.1–2.0 weight percent, is added to the α-olefin and the reactor is pressurized with BF$_3$ to about 5–100 psig, preferably 15–20 psig, at 20°–50 C., preferably 25°–35° C. The reaction is exothermic. Reactor composition can be monitored by subjecting samples to gas chromatography (GC). Preferably the reaction is continued until monomer concentration drops below about 5 weight percent. The reaction mixture at this stage will usually consist essentially of 0–5 weight percent monomer, 2–10 weight percent dimer, 20–50 weight percent trimer, 10–30 weight percent tetramer and the balance higher oligomers. Reaction time will be on the order of 0.5–4 hours.

Following the oligomerization reaction, the BF$_3$ catalyst is removed, usually by washing with water, preferably alkaline water. The monomer and dimer are too volatile to be of use in synlubes so the crude unsaturated oligomer is distilled to remove monomer and dimer. This is referred to as "topping" and the residue is a substantially dimer-free unsaturated oligomer sometimes referred to as topped unsaturated α-olefin oligomer.

Conventionally the entire distillation residue is hydrogenated and used as the synlube. This leads to excessive variation in viscosity and volatility properties of the hydrogenated synlube. In addition, the 100° C. viscosity is usually much too high to qualify as a "4 cs synlube", which is in high demand. When a higher viscosity synlube (e.g. 6 cs at 100° C.) is desired the topped hydrogenated oligomer can be distilled to remove a part of the trimer to leave a higher viscosity residue which can be used as a 6 cs synlube. This is shown in Cupples et al. U.S. Pat. No. 4,032,591. This process, however, gives a trimer fraction having a significant content of thermally cracked fragments which reduce its viscosity and flash point and increase its volatility. Furthermore, unsaturation is introduced causing an increase in bromine number in the trimer distillate. This makes the trimer fraction unsuitable for use in a low viscosity (e.g. 4 cs) synlube.

According to the present invention the topped unsaturated oligomer which consists essentially of trimer, tetramer, pentamer and higher oligomers is distilled prior to hydrogenation to obtain an unsaturated low viscosity fraction which consists mainly of trimer but can contain some tetramer (e.g. 0–10 weight percent) depending on how far the distillation is taken. This distillate fraction is subsequently hydrogenated to obtain a saturated low-viscosity α-olefin oligomer suitable for use in synlubes. The hydrogenated distillate fraction has much less unsaturation (i.e., a lower bromine number) and lower volatility compared to a corresponding saturated α-olefin distillate fraction which was hydrogenated prior to distillation. The synlube made by the present process also has a much higher flash point compared to a similar saturated oligomer distillate fraction made by the conventional process of hydrogenating prior to distillation.

Any α-olefin can be used in the process but preferably the α-olefin is a linear C$_{8-12}$ α-olefin. For use as an automotive synlube, 1-decene is by far the most preferred starting olefin. Optionally mixtures of α-olefin such as 1-octene, 1-decene and 1-dodecene can be used to arrive at a product having a viscosity suitable for use in an internal combustion engine.

The following examples show how the oligomerization reaction can be conducted. This is not part of the invention and is included only for the purpose of enablement.

EXAMPLE

In a reaction vessel was placed 2000 g of 1-decene and 12.0 g of n-butanol. The vessel was sealed and $BF_3$ gas introduced to raise the pressure to 20 psig. Stirring was continued at 30° C. under 20 psig $BF_3$ pressure for about 1.5 hours. The resultant oligomer was water-washed to remove $BF_3$ and alcohol. Analysis by GC gave the following composition:

|          |     |
|----------|-----|
| monomer  | 1%  |
| dimer    | 2%  |
| trimer   | 45% |
| tetramer | 32% |
| pentamer | 16% |
| hexamer  | 4%  |

The crude oligomer was topped by heating to 260° C. 6 torr to remove monomer and most of the dimer. By GC, the topped product contained 0.133 weight percent combined monomer and dimer. Other properties were:

|                      |         |
|----------------------|---------|
| Bromine No.          | 15.8    |
| Flash Point (open cup) | 226° C. |
| Noack Volatility[1]  | 6.4 wt %|

[1]Percent weight loss after 1 hour at 250° C. at 20 mm $H_2O$ vacuum.

The topped unsaturated oligomer was divided into 2 parts, A and B. Part A was hydrogenated at 199° C. under 400 psig $H_2$ using a nickel catalyst. Part A was then distilled to remove a trimer cut (99% trimer, 212°–245° C., 1.4 torr).

Part B was distilled prior to hydrogenation to remove a trimer cut (98% trimer, 209°–241 C., 0.6 torr). The Part B trimer cut was then hydrogenated at 193.3° C. under 400 psig hydrogen using a nickel catalyst. Both the A and B final products were analyzed to give the following results.

|                  | Part A Hydrogenate-Distill | Part B Distill-Hydrogenate |
|------------------|----------------------------|----------------------------|
| Viscosity 100° C.| 3.47 cs                    | 3.70 cs                    |
| 40° C.           | 2194 cs                    | 2320 cs                    |
| Bromine No.      | 0.96                       | 0.05                       |
| Flash Point      | 180° C.                    | 240° C.                    |
| Volatility       | 15.4                       | 12.5                       |

The results show that Part A was significantly degraded by the hydrogenate-distill sequence. Part A viscosity was substantially lower than Part B. Part A bromine number shows a substantial amount of olefinic unsaturation caused by cracking. This cracking lead to a sharp drop in flash point and an increase in volatility for the Part A product compared to the Part B product of this invention.

It seemed quite unexpected that the hydrogenated oligomer would be more subject to thermal degradation than the unsaturated oligomer. One would expect the opposite. In order to verify this observation, thermal stability tests were carried out on both an unsaturated and a saturated olefin oligomer. The test oligomer was made from 1-decene using a $BF_3$-n-butanol catalyst system as described in the previous example. The crude oligomer was topped to remove monomer and dimer and then distilled to separate a trimer fraction. The trimer fraction was hydrogenated at 200° C. under 400 psig hydrogen using a nickel catalyst. This gave a hydrogenated 1-decene trimer. The hydrogenated trimer was placed in a 2 L autoclave which was then purged with nitrogen and sealed. It was then heated to 312° C. over a 2-hour period. Pressure rose to 20 psig. After 9 minutes at 312°–320° C. it was cooled to 37° C. over 29 minutes. GC analysis were made before and after heat treatment.

In a similar manner a crude 1-decene oligomer was topped to remove monomer and dimer and distilled to obtain an unsaturated trimer fraction. The unsaturated trimer was placed in an autoclave which was flushed with nitrogen. The autoclave was sealed and heated to 312° C. over a 2-hour period. It was held at 312°–320° C. for about 10 minutes and then cooled to 37° C. over a 30-minute period. GC analysis were made before and after heat treatment.

The GC of unsaturated trimer were the same both before and after the heat treatment. However the GC analysis of the hydrogenated trimer after the heat treatment showed the formation of many very small peaks ahead of the main trimer fraction. Also an existing group of peaks right after the main fraction increased in height. The GC indicated that the unsaturated trimer remained substantially unchanged after the heat treatment but the hydrogenated trimer underwent some decomposition in the heat treatment. The present invention takes advantage of these observations by conducting the distillation on the unsaturated oligomer rather than distilling the hydrogenated oligomer.

We claim:

1. A process for preparing a saturated olefin oligomer fraction suitable for use as an internal combustion engine lubricant, said process comprising:
   (a) oligomerizing a $C_{8-12}$ α-olefin with a promoted $BF_3$ catalyst to obtain a crude unsaturated oligomer containing unsaturated monomer, dimer, trimer, tetramer and higher unsaturated oligomers,
   (b) distilling said crude unsaturated oligomer to remove said monomer and dimer leaving a substantially dimer-free unsaturated oligomer,
   (c) distilling said dimer-free unsaturated oligomer to obtain a distillate fraction containing at least 90 weight percent of trimer, and
   (d) hydrogenating said distillate fraction to obtain said saturated olefin oligomer.

2. A process of claim 1 wherein said crude unsaturated oligomer is an unsaturated o-decene oligomer.

3. A process of claim 1 wherein said dimer-free unsaturated oligomer also contains about 0.5–10 weight percent tetramer.

* * * * *